US 6,733,644 B2

(12) United States Patent
Yagi et al.

(10) Patent No.: US 6,733,644 B2
(45) Date of Patent: May 11, 2004

(54) GAS SENSOR AND GAS SENSOR UNIT

(75) Inventors: Hideaki Yagi, Aichi (JP); Takehiko Saiki, Gifu (JP); Keiichi Ichikawa, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 205 days.

(21) Appl. No.: 09/818,528

(22) Filed: Mar. 28, 2001

(65) Prior Publication Data

US 2001/0025787 A1 Oct. 4, 2001

(30) Foreign Application Priority Data

Mar. 29, 2000 (JP) ........................................ 2000-090285

(51) Int. Cl.[7] .............................................. G01N 27/41
(52) U.S. Cl. ........................................ 204/424; 204/425
(58) Field of Search ................................. 204/421–429

(56) References Cited

U.S. PATENT DOCUMENTS 3,843,400 A * 10/1974 Radford et al.
4,224,113 A * 9/1980 Kimura et al.
5,368,713 A * 11/1994 Friese et al.
5,866,799 A * 2/1999 Kato et al.

* cited by examiner

Primary Examiner—Kaj K. Olsen
(74) Attorney, Agent, or Firm—Sughrue Mion, PLLC

(57) ABSTRACT

A gas sensor includes a sensor element formed of a solid electrolyte having an oxygen ion conductivity; a cathode and an anode, each formed of a porous metal material and each formed on the sensor element, to produce a pumping current reflecting a concentration of a detection component in a measurement gas when a predetermined voltage is applied between the cathode and the anode. The detection component contains oxygen. The measurement gas contacts the cathode. The gas sensor also includes a gas diffusion control to vary the oxygen pumping current in accordance with a pressure of the measurement gas by controlling a diffusion of the measurement gas. The measurement gas moves from a measurement atmosphere toward the cathode by way of the gas diffusion control. Thereby, information on the pressure of the measurement gas is obtained based on the oxygen pumping current.

16 Claims, 14 Drawing Sheets

CROSS SECTION A-A

CROSS SECTION B-B

FIG.8(a)
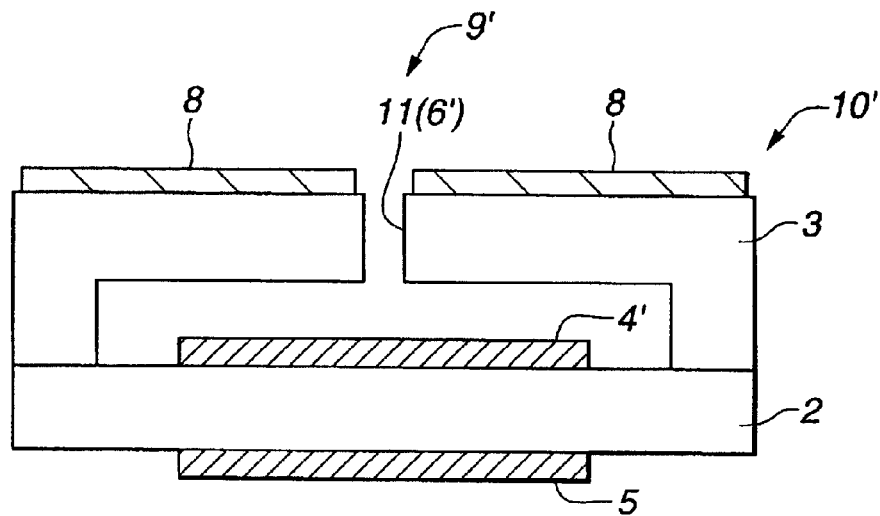
FIG.8(b)
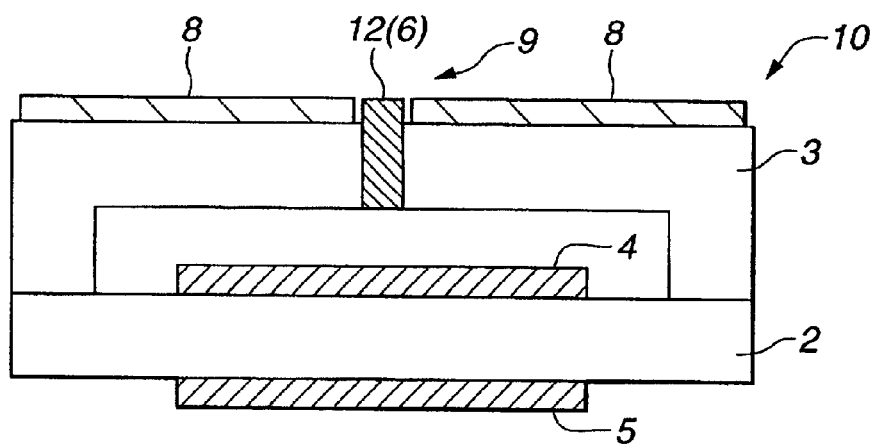
FIG.9
| $O_2$ CONCENTRATION=CO' | | | | 208 |
|---|---|---|---|---|
| PUMP CURRENT | $I_1$ | $I_2$ | $I_3$ | ..... |
| PRESSURE | $P_1$ | $P_2$ | $P_3$ | ..... |

FIG.10(a)

| PUMP CURRENT | $I'_1$ | $I'_2$ | $I'_3$ | ..... |
|---|---|---|---|---|
| $O_2$ CONCENTRATION ($CO_1$) | $CO_{11}$ | $CO_{12}$ | $CO_{13}$ | ..... |

| PUMP CURRENT | $I_1$ | $I_2$ | $I_3$ | ..... |
|---|---|---|---|---|
| $O_2$ CONCENTRATION ($CO_2$) | $CO_{21}$ | $CO_{22}$ | $CO_{23}$ | ..... |

| $\Delta CO$ \ $CO_1$ | $CO_{11}$ | $CO_{12}$ | $CO_{13}$ | ..... |
|---|---|---|---|---|
| $\Delta CO_1$ | $P_{11}$ | $P_{12}$ | $P_{13}$ | ..... |
| $\Delta CO_2$ | $P_{21}$ | $P_{22}$ | $P_{23}$ | ..... |
| $\Delta CO_3$ | $P_{31}$ | $P_{32}$ | $P_{33}$ | ..... |
| ⋮ | ⋮ | ⋮ | ⋮ | $\Delta CO = CO_1 - CO_2$ |

| $\Delta I$ \ $I'$ | $I'_1$ | $I'_2$ | $I'_3$ | ..... |
|---|---|---|---|---|
| $\Delta I_1$ | $P_{11}$ | $P_{12}$ | $P_{13}$ | ..... |
| $\Delta I_2$ | $P_{21}$ | $P_{22}$ | $P_{23}$ | ..... |
| $\Delta I_3$ | $P_{31}$ | $P_{32}$ | $P_{33}$ | ..... |
| ⋮ | ⋮ | ⋮ | ⋮ | $\Delta I = I'_1 - I_2$ |

CROSS SECTION C-C

GAS SENSOR AND GAS SENSOR UNIT

BACKGROUND OF THE INVENTION

The present invention relates in general to a gas sensor and a gas sensor unit using the gas sensor.

Conventionally, a limiting-type current gas sensor was used for detecting concentration of oxygen and steam in a measurement gas. The limiting-type current gas sensor is provided with a cathode and an anode. Each of the cathode and the anode is formed on a solid electrolyte for conducting oxygen ion, and is composed of a porous electrode. The cathode of the limiting-type current gas sensor is provided with a gas diffusion control which is composed of a cover having a small hole, or composed of a porous body. With the thus provided gas diffusion control, the gas diffusion moving from a measurement atmosphere toward the cathode can be controlled. For example, when a gas in the measurement atmosphere contains oxygen, the oxygen is sent to the cathode through the gas diffusion control. At this point in time, if a proper voltage is applied between the cathode and the anode, the oxygen that is dissociated on the cathode is ionized and then is flowed toward the anode in the solid electrolyte. The current caused by the ionized oxygen is called a pumping current. The thus obtained pumping current is saturated at the limiting current value, which is obtained when diffusion rate of the oxygen passing through the gas diffusion control reaches a controlled value. It is known that the limiting current value is substantially proportional to the oxygen concentration in the gas.

In this case, what is measurable is not limited to the concentration of molecular oxygen. For example, concentration of water (steam) is also measurable in the following manner, provided that the water (steam) contains oxygen atom in its molecule: Increase the voltage between the anode and the cathode to such an extent that an electrolysis of the molecular water (steam) is caused, to thereby cause the limiting current. With the thus obtained limiting current, the concentration of the water (steam) is measurable. This summarizes that the limiting-type current gas sensor is not limited to measurement of oxygen concentration. More specifically, the limiting-type current gas sensor is also used for measuring steam concentration (or partial pressure) in an exhaust gas from general purpose internal combustion engines such as boiler and the like. However, no art is provided or even proposed that is capable of measuring atmospheric pressure, altitude and the like by means of such gas sensor.

SUMMARY OF THE INVENTION

It is, therefore, an object of the present invention to provide a gas sensor that is capable of detecting pressure of a measurement gas.

It is another object of the present invention to provide a sensor unit that is capable of outputting pieces of information on an atmospheric pressure, altitude and the like by means of the gas sensor.

There is provided a gas sensor, according to the present invention. The gas sensor comprises: a sensor element formed of a solid electrolyte having an oxygen ion conductivity; a cathode and an anode, each formed of a porous metal material and each formed on the sensor element, to produce a pumping current reflecting a concentration of a detection component in a measurement gas when a predetermined voltage is applied between the cathode and the anode, the detection component comprising oxygen, the measurement gas contacting the cathode; and a gas diffusion control to vary the oxygen pumping current in accordance with a pressure of the measurement gas by controlling a diffusion of the measurement gas, the measurement gas moving from a measurement atmosphere toward the cathode by way of the gas diffusion control, to thereby obtain information on the pressure of the measurement gas based on the oxygen pumping current.

Moreover, there is provided a sensor unit, according to the present invention. The sensor unit comprises a pressure sensor. The pressure sensor comprises: a sensor element formed of a solid electrolyte having an oxygen ion conductivity; a cathode and an anode, each formed of a porous metal material and each formed on the sensor element, to produce a pumping current reflecting a concentration of a detection component in a measurement gas when a predetermined voltage is applied between the cathode and the anode, the detection component comprising oxygen, the measurement gas contacting the cathode; and a gas diffusion control to vary the oxygen pumping current in accordance with a pressure of the measurement gas by controlling a diffusion of the measurement gas, the measurement gas moving from a measurement atmosphere toward the cathode by way of the gas diffusion control, to thereby obtain information on the pressure of the measurement gas based on the oxygen pumping current. The sensor unit generates and outputs information on an atmospheric pressure and an altitude based on the information on the pressure obtained by the pressure sensor.

BRIEF DESCRIPTION OF THE DRAWINGS

FIG. 5 is a detecting element 10' having a first electrode 4', in which

FIG. 5(*a*) is a perspective view of the detecting element 10', and

FIG. 5(*b*) is a cross sectional view of the detecting element 10', taken along lines B—B in FIG. 5(*a*);

FIG. 8 is a cross section of the gas sensor 1 with a second modification, in which;

FIG. 8(*a*) has a gas diffusion control 9' having a gas vent 11, and

FIG. 8(*b*) has a gas diffusion control 9 having a porous body 12;

FIG. 9 shows a table 208 concerning an oxygen pumping current I relative to a pressure P;

FIG. 10 shows four tables, in which

FIG. 10(*a*) is a table 210 concerning an oxygen pumping current I' relative to an oxygen concentration $CO_1$, FIG. 10(*b*) is a table 212 concerning the oxygen pumping current I relative to the oxygen concentration $CO_2$, FIG. 10(c) is a table 214 concerning the pressure P with respect to the oxygen concentration $CO_1$ relative to a oxygen concentration difference $\Delta CO$ ($\Delta CO = CO_1 - CO_2$), FIG. 10(d) is a table 216 concerning the pressure P with respect to the oxygen pumping current I' relative to a current difference $\Delta I$ ($\Delta I = I' - I$);

FIG. 11 shows two tables in which,

FIG. 12 is a gas sensor 100 with a third modification in which,

DETAILED DESCRIPTION OF THE PREFERRED EMBODIMENT

Figure 1:
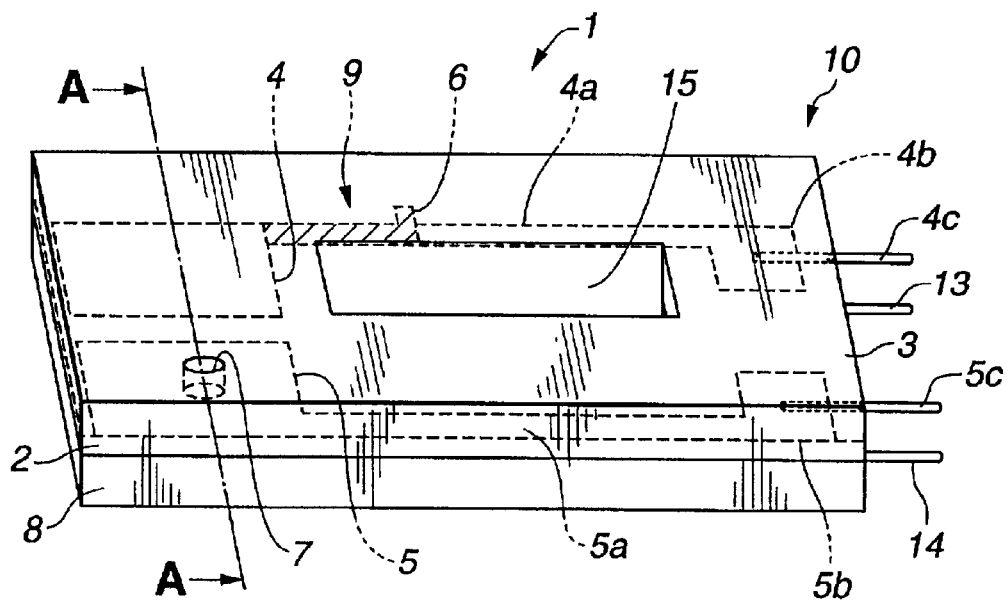
FIG. 1 is a perspective view of a gas sensor 1 under the present invention.
Figure 2:
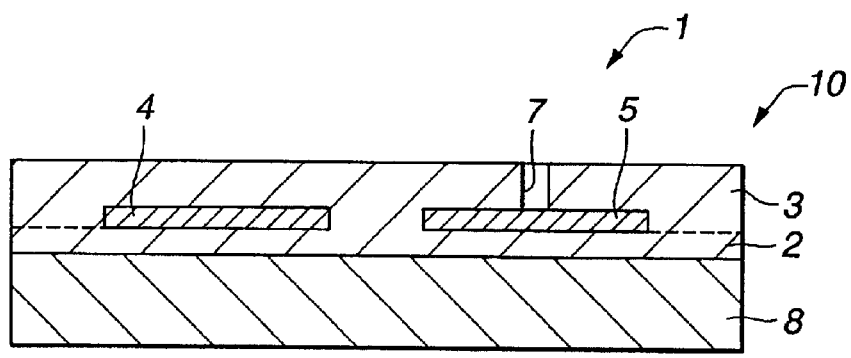
FIG. 2 is a cross section taken along lines A—A in FIG. 1, in which a sensor element 2 and a gas blockage 3 are composed of substantially the same solid electrolyte.

As is seen in FIG. 1, there is provided a gas sensor 1, according to a preferred embodiment of the present invention. FIG. 1 shows a perspective view of the gas sensor 1. FIG. 2 shows a cross section A—A in FIG. 1.

The gas sensor 1 is provided with a sensor element 2, a cathode 4, an anode 5, a cathode lead 4a, an anode lead 5a, a gas introducing portion 6, a gas blockage 3, a heater element 8, and the like.

The sensor element 2 is formed substantially into a plate. The cathode 4 and the anode 5 are formed on the sensor element 2. The cathode lead 4a and the anode lead 5a energize, respectively, the cathode 4 and the anode 5. The gas introducing portion 6 is branched from the cathode lead 4a. The gas blockage 3 is substantially a plate member, and is so laminated on the sensor element 2 as to cover the cathode 4, the anode 5, the cathode lead 4a, the anode lead 5a and the gas introducing portion 6. The heater element 8 is substantially a plate, and is laminated from an opposite side of the gas blockage 3 with respect to the sensor element 2.

The sensor element 2 is composed of a solid electrolyte having an oxygen ion conductivity. Included typically in such solid electrolytes are a solid solution of $ZrO_2$ and $Y_2O_3$, and a solid solution of $ZrO_2$ and $CaO$. Other types of solid solutions are allowed; such as $ZrO_2$ and oxide of another alkaline earth metal, or $ZrO_2$ and oxide of another rare earth metal. The $ZrO_2$ (base material) is allowed to include $HfO_2$.

Figure 3:
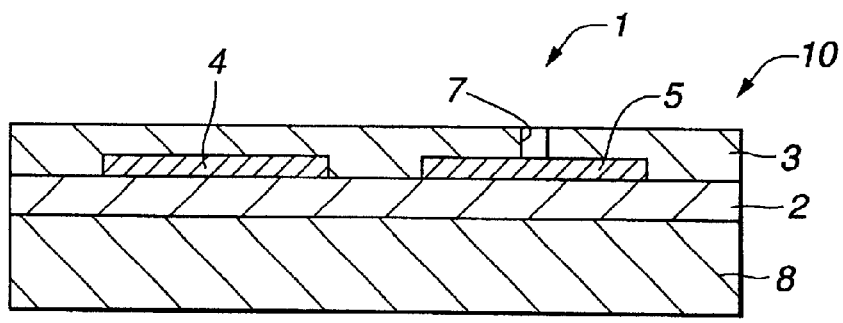
FIG. 3 is a cross section of the gas sensor 1 with a first modification, namely, similar to FIG. 2 but the sensor element 2 and the gas blockage 3 composed of ceramics which are made of different materials from each other.

In this preferred embodiment, the sensor element 2 is formed substantially into a plate having dimensions such as thickness of 0.15 mm, width of 5 mm and length of 23 mm. On the other hand, the gas blockage 3 is composed of the same solid electrolyte as that of the sensor element 2. Also the gas blockage 3 has the same width (5 mm) and length (23 mm) as those of the sensor element 2. The sensor element 2 and the gas blockage 3 are integrated through firing, to thereby form a detecting element 10 which is an integrated layered body. In this embodiment, the total thickness of the detecting element 10 is approximately 0.3 mm. As is seen in FIG. 3 (first modification), the gas blockage 3 is allowed to be composed of a ceramic that is made of material different from the one used for the sensor element 2, provided that such ceramic is free of gas permeability. For example the gas blockage 3 is allowed to be composed of $Al_2O_3$ and the like.

Each of the cathode 4 and the anode 5 is composed of a porous body made of Pt (platinum) or Pt alloy (hereinafter referred to as "Pt porous body"), and is disposed at a first end of the sensor element 2 in a longitudinal direction of the sensor element 2. The cathode 4 and the anode 5 are disposed adjacent to each other in a widthwise direction of the sensor element 2. In this preferred embodiment, each of the cathode 4 and the anode 5 is formed into a rectangle having a thickness of about 20 $\mu m$, a width of about 1 mm and a length of about 3 mm. On the other hand, each of the cathode lead 4a and the anode lead 5a is composed of Pt porous body, and is formed into a strip having a width smaller, respectively, than the cathode 4 and the anode 5. Moreover, each of the cathode lead 4a and the anode lead 5a has a first end connected, respectively, to the cathode 4 and the anode 5, and a second end extending in the widthwise direction of the sensor element 2. The second end of each of the cathode lead 4a and the anode lead 5a is formed, respectively, into a terminal connection 4b and a terminal connection 5b having a width a little greater, respectively, than the cathode lead 4a and the anode lead 5a. There are provided a terminal 4c and a terminal 5c. Each of the terminal 4c and the terminal 5c is made of Pt, and is formed substantially into a wire. Moreover, each of the terminal 4c and the terminal 5c has a first end which is connected, respectively, to the terminal connection 4b and the terminal connection 5b in such a manner as to be interposed between the sensor element 2 and the gas blockage 3, and has a second end projecting from an end surface of the detecting element 10. The anode 5 is allowed to be composed of a porous body made of Pd (palladium) or Pd alloy (hereinafter referred to as "Pd porous body").

From substantially a middle portion of the cathode lead 4a, there is provided a branch 6 which is formed into a strip and branches sideward. The branch 6 is composed of one of the Pt porous body and the Pd porous body. As is seen in FIG. 1, the branch 6 has a first end which is exposed on a side surface of the detecting element 10. At the first end of the branch 6 exposed, the branch 6 is formed into a gas hole for introducing gas. Thereby, the branch 6 together with the cathode lead 4a constitute a gas diffusion control 9 that leads measurement gas to the cathode 4. During the time the measurement gas is led by the gas diffusion control 9, the measurement gas is also controlled by means of the gas diffusion control 9 in terms of its diffusion rate.

On the other hand, the gas blockage 3 has a gas outlet 7 which is disposed in a position corresponding to the anode 5, and communicates the anode 5 with an outside area. The gas outlet 7 is not particularly restricted in terms of cross sectional shape, provided that the gas outlet 7 is capable of communicating the anode 5 with the outside area, and that the cross section of the gas outlet 7 is greater in size than the gas introducing portion 6.

Figure 4:
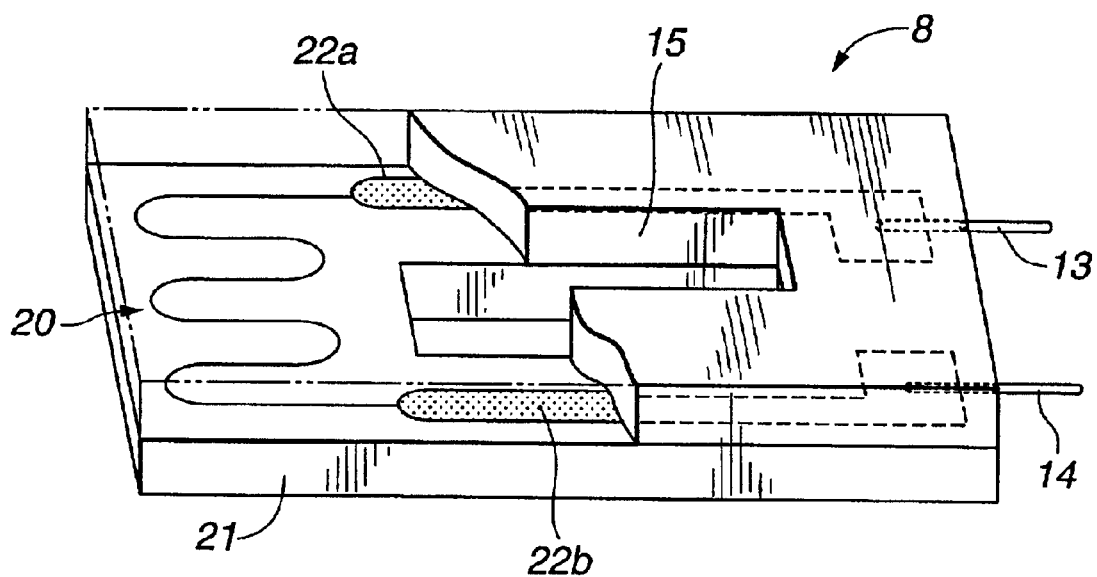
FIG. 4 is a partly broken perspective view of a heater element 8 used for the gas sensor 1 in FIG. 1.

As is seen in FIG. 4, the heater element 8 is so formed that a resistance exothermic portion 20 is embedded in a ceramic base 21. The ceramic base 21 is composed of $Al_2O_3$ and the like, and is formed substantially into a plate. The resistance exothermic portion 20 is formed substantially into a wire, which is composed of Pt and the like, and positioned at a position corresponding to the cathode 4 and the anode 5 of the sensor element 2. The resistance exothermic portion 20 is energized and heated by a lead 22a and a lead 22b, and moreover, energized and heated by a terminal 13 and a terminal 14 which are connected, respectively, to an end of the lead 22a and the lead 22b. The resistance exothermic portion 20 acts as a local area heater. More specifically, it is only the above mentioned position corresponding to the cathode 4 and the anode 5 of the sensor element 2 that the resistance exothermic portion 20 heats. The gas sensor 1 according to the preferred embodiment is constituted of the heater element 8 and the aforementioned detecting element 10 laminated on the heater element 8, and is shaped substantially into a plate. There is provided a gas vent 15 at substantially a middle portion of the gas sensor 1. The gas vent 15 penetrates through the laminating direction of the heater element 8 and the detecting element 10.

The above gas sensor 1 is produced, for example, in the following steps and manners.

At first, the heater element 8 is formed in the following steps and manners: On an upper surface of a first green sheet composed of $Al_2O_3$ powder, form printing patterns which become the resistance exothermic portion 20, the lead 22a, and the lead 22b (In this case, it is Pt paste that is used for the printing patterns. And, the first green sheet has an opening which becomes the gas vent 15 after firing.). Then, put a Pt wire (for each of the terminal 13 and the terminal 14) on a second end (right end in FIG. 4) of the printing pattern, respectively, of the lead 22a and the lead 22b. Then, laminate a second green sheet composed of $Al_2O_3$ powder having the same feature as that of the first green sheet. Then, fire the thus laminated first and second green sheets for integration.

On the other hand, the detecting element 10 is formed in the following steps and manners: Form printing patterns which become the cathode 4 and the anode 5 on an upper surface of a first green sheet composed of a first solid electrolyte (In this case, it is one of Pt paste and Pt alloy paste that is used for the printing patterns.). Moreover, form printing patterns which become the cathode lead 4a of the cathode 4 and the anode lead 5a of the anode 5, using the Pt paste. Then, put the Pt wire (for each of the terminal 4c and the terminal 5c) on a second end (right end in FIG. 1) of the printing pattern, respectively, of the cathode lead 4a and the anode lead 5a. Then, laminate a second green sheet composed of a second solid electrolyte on the first green sheet. Then, fire the thus laminated first and second green sheets at about 1,500° C. for integration.

The thus obtained heater element 8 and detecting element 10 are joined together with each other by means of a sealing glass, an inorganic adhesive and the like, to thereby form the gas sensor 1 as is seen in FIG. 1.

The gas diffusion control 9 is formed with the porous body. Allowing pores of the gas diffusion control 9 to have bore diameters in a range from 100 angstrom (0.01 $\mu$m) to 1 $\mu$m can cause the Knudsen diffusion around the gas diffusion control 9. The Knudsen diffusion is dependent on pressure of the measurement gas. Thereby, the cathode 4 generates an electric current value that parameterizes an oxygen concentration and a pressure. Especially, in the case of atmosphere whose oxygen concentration is known (in other words, the oxygen concentration parameter can be regarded as a known constant), an oxygen pumping current value generated can correspond to the pressure of the measurement gas substantially on one-to-one basis. Therefore, a pressure value of the measurement gas can be obtained by detecting the oxygen pumping current.

On the other hand, pores of the gas diffusion control 9 having a bore diameter below 100 angstrom (0.01 $\mu$m) is likely to cause a diffusion decrease, to thereby worsens response to pressure fluctuations and the like.

Contrary to this, pores of the gas diffusion control 9 having a bore diameter exceeding 1 $\mu$m is likely to cause a free diffusion so that the diffusion has a reduced pressure dependency. Thereby, it becomes less likely to obtain effective correlation between the generated current value and the atmospheric pressure.

The gas diffusion control 9 preferably controls change (detected oxygen concentration to oxygen concentration at gauge pressure of 0 kPa) of 10% or over, under the following two conditions: 1. Measurement is carried out under a constant oxygen concentration. 2. Measurement atmosphere is variable in a range from −60 kPa to 0 kPa at gauge pressure. With this, the gas sensor's response (namely, current change) to the pressure change becomes great, to thereby diminish measurement errors. This contributes toward obtaining more accurate pressure values. In this preferred embodiment, adjusting the bore diameter of the gas vent enables diffusion control so that the above oxygen concentration change becomes 10% or over.

Figure 5A:
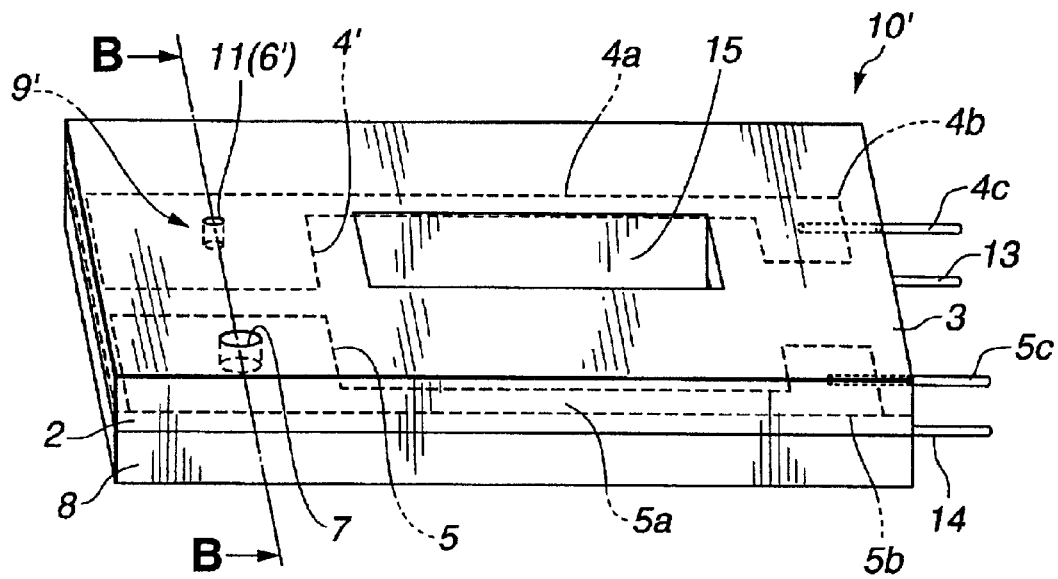
Figure 5B:
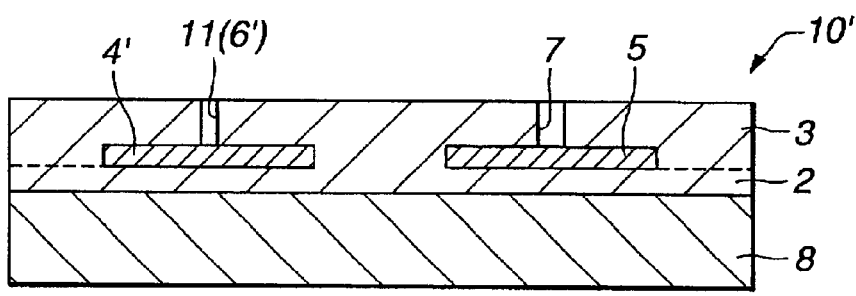

As is seen in FIG. 5, there is provided a detecting element 10'. The detecting element 10' has substantially a similar constitution to that of the detecting element 10 in FIG. 1. Stated below are only differences of the detecting element 10' as compared with the detecting element 10.

The detecting element 10' is formed with a gas diffusion control 9' having a diffusing power which is different from that of the gas sensor 1 in FIG. 1. As is seen in the cross section B—B in FIG. 5(a) and FIG. 5(b), the gas diffusion control 9' has a gas vent 11. The gas vent 11 acts as a gas introducing portion 6', and has a bore diameter which is so adjusted as to introduce the measurement gas under a free diffusion condition. The gas vent 11 is so formed as to penetrate through the gas blockage 3 and introduce the measurement gas to a cathode 4'. The gas vent 11 has a bore diameter in a range from 3 $\mu$m to 3,000 $\mu$m. With the bore diameter range described above, the measurement gas has a small pressure dependency (in other words, diffusion whose pressure dependency ignorable) around the gas diffusion control 9'. Thereby, the oxygen pumping current detected is regarded as to correspond to the oxygen concentration substantially on one-to-one basis.

On the other hand, the bore diameter of the gas vent 11 below 3 $\mu$m will cause the measurement gas to be dependent on pressure (in other words, diffusion changeable according to pressure of measurement gas).

Contrary to this, the bore diameter of the gas vent 11 exceeding 3,000 $\mu$m will disable the gas sensor 1 from acting as a limiting-type current sensor. Thereby, the pumping current value that is dependent on oxygen concentration becomes less likely to be obtained.

Figure 6:
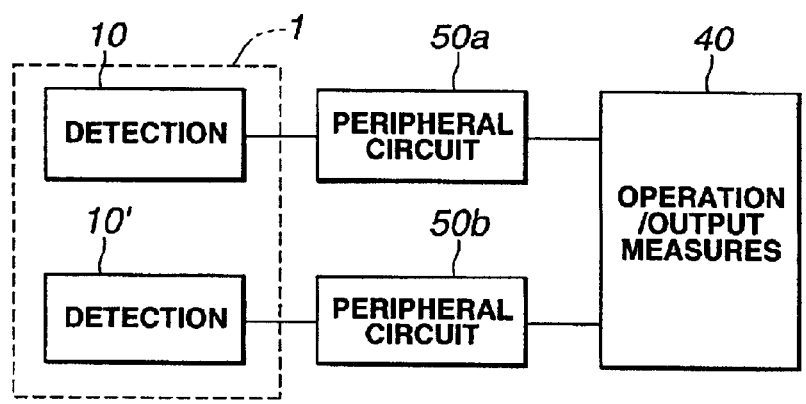
FIG. 6 is a schematic block diagram of a gas sensor system under the present invention.

Moreover, there is provided the gas sensor 1 having a constitution as is schematically seen in FIG. 6.

The gas sensor 1 in FIG. 6 includes the detecting element 10 and the detecting element 10' as are seen, respectively, in FIG. 1 and FIG. 5. In other words, a plurality of cathodes (Namely, two or more cathodes. In FIG. 6, a second cathode 4 and a first cathode 4') are provided as different pressure dependency electrodes. There are provided the gas diffusion control 9 and the gas diffusion control 9'. A gas diffusion resistance of each of the gas diffusion control 9 and the gas diffusion control 9' is so adjusted that the gas diffusion control 9 and the gas diffusion control 9' become different from each other, in terms of the pressure dependency of the outputted oxygen pumping current, corresponding to one of the respective different pressure dependency electrodes 4' and 4. Pressure information of the measurement gas is generated based on the oxygen pumping current which is outputted from each of the different pressure dependency electrodes 4 and 4'.

More specifically, the different pressure dependency electrodes include the first cathode 4' and the second cathode 4 whose outputted oxygen pumping current is more pressure dependent than that of the first cathode 4'. For example, the gas sensor 1 is allowed to be so constituted that the difference in outputted oxygen pumping current between the first cathode 4' and the second cathode 4 is used as output of the pressure information. Thereby, even when the oxygen concentration of the measurement gas fluctuates, the pressure of the measurement gas can be accurately measured. In other words, since the different pressure dependency electrodes are plural (two or more) in number, the output values can be obtained plural (two or more) in number, which output values parameterizing two unknown quantities, that is, oxygen concentration and pressure of the measurement gas. Thereby, even when the oxygen concentration is unknown, pressure values can be obtained based on the thus obtained output values.

Moreover, together with the information on the pressure of the measurement gas, information on the oxygen concentration of the measurement gas is also made obtainable, based on the oxygen pumping current values which are outputted from each of the different pressure dependency electrodes. For example, as is seen in FIG. 5, the outputted oxygen pumping current value of the first cathode 4' that has a small pressure dependency can be made obtainable (output) as the information on oxygen concentration of the measurement gas. With this, the information on the oxygen concentration and the information on the pressure can be generated together, thus improving usefulness. The detecting element used for detecting the oxygen concentration (in this embodiment, the detecting element 10' having the first cathode 4') is preferably the one that controls change (detected oxygen concentration to oxygen concentration at gauge pressure of 0 kPa) of 5% or below (more preferably, 2% or below), under the following two conditions: 1. Measurement is carried out under a constant oxygen concentration. 2. Measurement atmosphere is variable in a range from −60 kPa to 0 kPa at gauge pressure.

As is seen in FIG. 8(a) and FIG. 8(b) (second modification), the gas sensor under the present invention is allowed to be formed in such a manner that the first cathode 4' and the anode 5 are separately disposed, respectively, on upper and lower sides of the sensor element 2, while the second cathode 4 and the anode 5 are separately disposed, respectively, on the upper and lower sides of the sensor element 2. For the detecting element 10' having the first cathode 4', the gas diffusion control 9' is constituted of a cover defining the gas vent 11 (a small opening which becomes the gas introducing portion 6') opened. On the other hand, for the detecting element 10 having the second cathode 4, there is provided the porous body 12 acting as the gas introducing portion 6. The measurement gas is introduced to the second cathode 4 by way of the porous body 12. The porous body 12 preferably has a bore diameter that has a range wide enough for satisfactory pressure dependency, in other words, as wide as the bore diameter of the gas diffusion control 9 in FIG. 1.

Stated below are fundamental operations of the gas sensor 1.

At first, for example, the gas sensor 1 shown in FIG. 1 is put in a measurement atmosphere. Then, the heater element 8 is energized, to thereby heat the sensor element 2 to a predetermined operation temperature (active temperature: for example 500° C.). Then, the measurement gas in the measurement atmosphere is introduced to the cathode 4 by way of the gas diffusion control 9 as is seen in FIG. 1. During the introduction, diffusion of the measurement gas is controlled. Then, under this condition, a predetermined voltage is applied between the anode 5 and the cathode 4. Thereby, the oxygen is dissociated that is maintained at the gas hole of the cathode 4 composed of Pt porous body. Then, the thus dissociated oxygen is pumped in the sensor element 2 from the cathode 4 toward the anode 5, to thereby cause a pumping current corresponding to the oxygen concentration in the measurement gas. At this point in time, it is only in the vicinity of the cathode 4 that is heated in the sensor element 2 (namely, local heating). The portion corresponding to the gas diffusion control 9 is not so heated as to exhibit oxygen ion conductivity. Therefore, according to progress of the pumping, a new gas is supplied to the cathode 4 by way of the gas diffusion control 9. At this point in time, the oxygen throughput passing through the gas diffusion control 9, namely, oxygen volume supplied to the cathode 4 is influenced by pressure of the measurement gas, to thereby generate oxygen pumping current which is dependent on pressure.

Moreover, the present invention is allowed to relate to a gas sensor unit having the following system. Stated below is about the sensor system using the gas sensor 1 in FIG. 1 and some structural examples related thereto.

Figure 7:
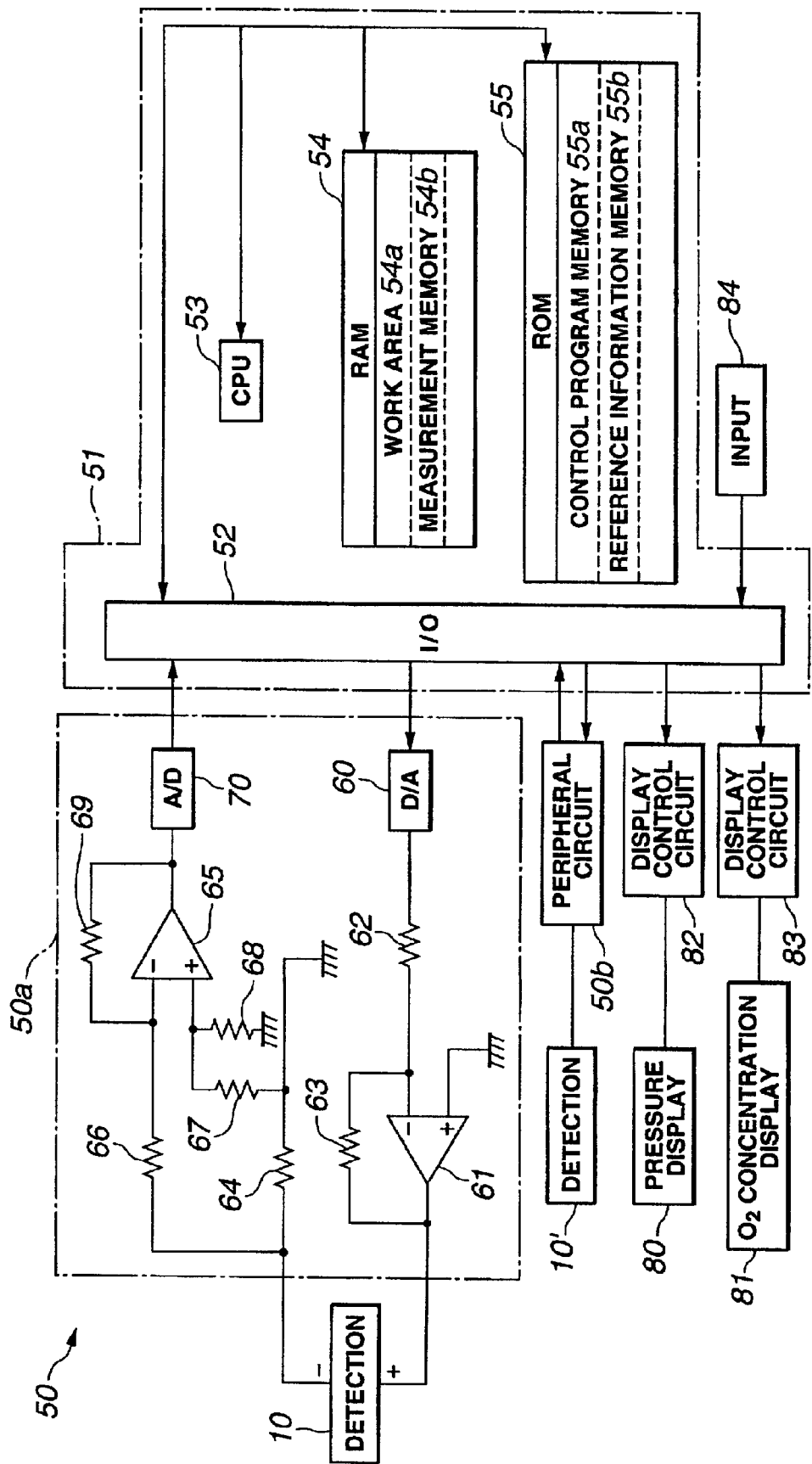
FIG. 7 is a detailed block diagram of an electrical constitution of the gas sensor system.

As is seen in FIG. 7, there is provided a block diagram showing an example of an electrical constitution of a sensor system 50. In other words, the sensor system 50 is constituted of the gas sensor 1 (see FIG. 1) equipped with the detecting element 10, a microprocessor 51, and a peripheral circuit 50a for connecting the gas sensor 1 and the microprocessor 51.

There is provided an operation amplifier 61 which acts as a power source, and is connected to the anode 5 of the gas sensor (FIG. 1). A command voltage is inputted to the operation amplifier 61 from the microprocessor 51 by way of a digital-to-analogue converter 60 (hereinafter referred to as "D/A converter 60"). The operation amplifier 61 applies to the anode 5 a voltage corresponding to the value of the command voltage. On the other hand, the cathode 4 of the gas sensor 1 is connected to ground by way of a resistor 64 for current detection. Voltages at both ends of the resistor 64 are inputted to an operation amplifier 65 which constitutes a differential amplifier together with peripheral resistors such as a resistor 66, a resistor 67, a resistor 68, and a resistor 69. An output from the operation amplifier 65 is inputted to the microprocessor 51 by way of an analogue-to-digital converter 70 (hereinafter referred to as "A/D converter 70"). The output thus inputted to the microprocessor 51 acts as information on pumping current flowing into the gas sensor 1. The heater element 8 of the gas sensor 1 is connected to a heater power source (not shown) by way of an energizing control circuit. Exothermic heat of the heater element 8 is controlled by, for example, pulse width modulation (hereinafter referred to as "PWM") so that the above sensor element 2 is heated to a sensor operation temperature.

As is seen in FIG. 7, the microprocessor 51 is constituted of an input-output port 52 (hereinafter referred to as "I/O port 52"), a CPU 53, a RAM 54, a ROM 55 and the like. The I/O port 52 acts as an input-output interface between the microprocessor 51 and the peripheral circuit 50a, and is connected to the CPU 53, the RAM 54, and the ROM 55. There are provided a work area 54a, and a measurement memory 54b in the RAM 54. The work area 54a is of the CPU 53, and the measurement memory 54b memorizes data of various measured values which are taken in during an aftermentioned transaction, or data of various measured values arising during the course of an aftermentioned control transaction. In the ROM 55, there are formed a control program memory 55a, and a reference information memory 55b. The control program memory 55a operates to determine output values of detected element of the sensor system 50, and memorizes control program which commands output control. The reference information memory 55b stores reference information used by the control program 55a. Details of the reference information memory 55b is mentioned afterwards. The CPU 53 functions as measures such as for determining the oxygen concentration and the pressure based on the above control program, and for controlling output information on the oxygen concentration and the pressure.

Moreover, as is seen in FIG. 7, there are provided a pressure display 80 and an oxygen concentration display 81 which are connected to the I/O port 52 by way of, respectively, a display control circuit 82 and a display control circuit 83. The pressure display 80 is constituted of seven segment light emitting diode (LED), liquid crystal display and the like, and displays pieces of information on pressure of the measurement gas such as atmospheric pressure, altitude and the like. The oxygen concentration display 81 displays pieces of information on oxygen concentration of the measurement gas such as oxygen concentration values and the like.

Stated below are about operations of the sensor system 50. Chiefly explained is flow of transactions by the CPU 53 of the microprocessor 51. Firstly, the gas sensor 1 (in FIG. 1 and the like) is disposed in the measurement atmosphere. The heater element 8 is energized so as to heat the heater element 8 to the operation temperature. Then, the voltage is set at a predetermined voltage value, which voltage is to be applied to both the cathode 4 and the anode 5 of the gas sensor 1. The pumping current I at this point in time is a first limiting current, and corresponds to the oxygen concentration in the measurement atmosphere and to the pressure of the measurement atmosphere. If the gas sensor 1 is used in an environment where the oxygen concentration is constant (for example, used in an atmosphere), the current output value corresponds to the pressure. Therefore, if the current value is known, the pressure value can be obtained by referring to a table 208 as is seen in FIG. 9. The table 208 is stored in the reference information memory 55b. The table 208 is allowed to be so constituted as to reflect the pumping current values corresponding to the pressure values under the constant oxygen concentration. For example, assume that the sensor system 50 is used in the atmosphere. In this case, the current values corresponding to the pressure values can be obtained provided that the table 208 is so constituted that the pumping current values correspond to the pressure values under the oxygen concentration of the atmosphere.

Therefore, in an environment where the oxygen concentration makes no change, the pressure can be measured in no need of complicated constitutions. Thus, the sensor system 50 is useful, for example, for an altimeter and the like.

As is seen in FIG. 6, there are provided a plurality of detecting elements (i.e. 10 and 10'). In this case, in addition to a piece of input information from the detecting element 10, another piece of input information from the detecting element 10' is to be referred to. As is seen in FIG. 7, the detecting element 10' is connected to the peripheral circuit 50b which is connected to the I/O port 52. The peripheral circuit 50b is allowed to have a constitution substantially the same as that of the peripheral circuit 50a, to thereby form a constitution that is capable of detecting oxygen pumping current values generated at the detecting element 10'.

Information on the oxygen pumping current generated at each of the detecting element 10 and the detecting element 10' is inputted to the I/O port 52. With the thus inputted information, predetermined operations are carried out, to thereby obtain information on pressure of the measurement gas.

An oxygen pumping current I at the second cathode 4 is detected by the detecting element 10, while an oxygen pumping current I' at the first negative element 4' is detected by the detecting element 10'. As is seen in FIG. 10(a) and FIG. 10(b), there are provided a table 210 and a table 212 which are stored in the reference information memory 55b based, respectively, on the oxygen pumping current I and the oxygen pumping current I'. Each of FIG. 10(a) and FIG. 10(b) has a table constitution with which the oxygen concentration can be obtained. The above oxygen concentration is the one that is introduced into each of the first negative element 4' and the second cathode 4 in a form corresponding to the generated current of one of the first negative element 4' and the second cathode 4. More specifically, when the oxygen pumping current at the first cathode 4' can be regarded to be independent of the pressure of the measurement gas, the current value at the first cathode 4' and the oxygen concentration of the measurement gas can be regarded to make one-to-one correspondence. Thereby, the thus corresponding data is stored in the table 210 in FIG. 10(a). Therefore, once the oxygen pumping current I' of the first cathode 4' is determined, the oxygen concentration CO of the measurement gas can be obtained. In other words, the outputted oxygen pumping current values of the first cathode 4' can be outputted as information on the oxygen concentration of the measurement gas.

The oxygen pumping current I which is greatly dependent on pressure is generated at the second cathode 4. The oxygen pumping current I exhibits an oxygen concentration value that depends on pressure of the measurement gas. As is seen in FIG. 10(b), a table 212 shows the oxygen concentration values detected at the second cathode 4.

As is seen in FIG. 10(c), there is provided a table 214 for calculating pressure based on the oxygen concentration which is obtained by each of the different pressure dependency electrodes. More specifically, the table 214 calculates the pressure of the measurement gas based on the following two factors: One is the detected oxygen concentration of the measurement gas. The other is a difference in oxygen concentration between the first cathode 4' and the second cathode 4. Stated below is an example. In this example, as stated above, assume that the oxygen concentration can be measured at the first cathode 4' (in other words, the pressure of the measurement gas is ignorable at the first cathode 4' as stated above). The detected oxygen concentration $CO_1$ at the first cathode 4' is defined as oxygen concentration of the measurement gas. $CO_2$ is the detected oxygen concentration at the second cathode 4. Then, the pressure P of the measurement gas can be obtained by an oxygen concentration difference $\Delta CO$ that is obtained by subtracting $CO_2$ from $CO_1$ ($\Delta CO = CO_1 - CO_2$). On the other hand, as is seen in FIG. 10(d), there is provided a table 216 for calculating the pressure P based on the following two factors: One is the oxygen pumping current I' at the first cathode 4'. The other is a current difference $\Delta I$ that is obtained by subtracting the oxygen pumping current I at the second cathode 4 from the oxygen pumping current I' at the first cathode 4' ($\Delta I = I' - I$).

Figure 11A:
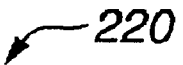
FIG. 11(a) is a table 220 concerning the oxygen pumping current I' with respect to the pressure P relative to the oxygen concentration CO.
Figure 11B:
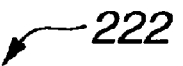
FIG. 11(b) is a table 222 concerning the oxygen pumping current I with respect to the pressure P relative to the oxygen concentration CO.

As is seen in FIG. 11(a), there is provided a table 220 showing the oxygen pumping current I' generated at the first cathode 4' which parameterizes the oxygen concentration CO of the measurement gas and the pressure P. Moreover, as is seen in FIG. 11(b), there is provided a table 222 showing the oxygen pumping current I generated at the second cathode 4 which parameterizes the oxygen concentration CO of the measurement gas and the pressure P.

With the table 220 and the table 222, each of the oxygen concentration CO and the pressure P can be obtained which satisfy both the oxygen pumping current I' and the oxygen pumping current I. Stated below are the steps of operations for example: At first, search the table 220 for a combination of CO and P satisfying the oxygen pumping current I'. Then, refer to the table 222 in FIG. 11(b) in terms of the oxygen pumping current I for the thus searched combination of CO and P. Then, search for a combination of CO and P corresponding to the oxygen pumping current I that is the same as (or the nearest to) the oxygen pumping current I detected at the second cathode 4. Use the thus searched combination of CO and P as a measured value of the gas. Each of the tables shown in FIG. 9 through FIG. 11 is allowed to be stored in the reference information memory 55b in FIG. 7.

In any case, information on the calculated pressure can be displayed on the pressure display 80 by way of the display control circuit 82 in FIG. 7, while information on the calculated oxygen concentration can be displayed on the oxygen concentration display 81 by way of the display control circuit 83 in FIG. 7. Under the present invention, the pressure is displayed on the pressure display 80, while the oxygen concentration is displayed on the oxygen concentration display 81. However, the present invention is not limited to this. For example, information on the measured pressure and the oxygen concentration can be outputted from the I/O port 52 as signal. Such output signal is allowed to vary. For example, a digital signal can be transmitted to various other devices, or an analogue signal converted by way of a D/A converter can be transmitted to the various other devices.

Figure 12A:
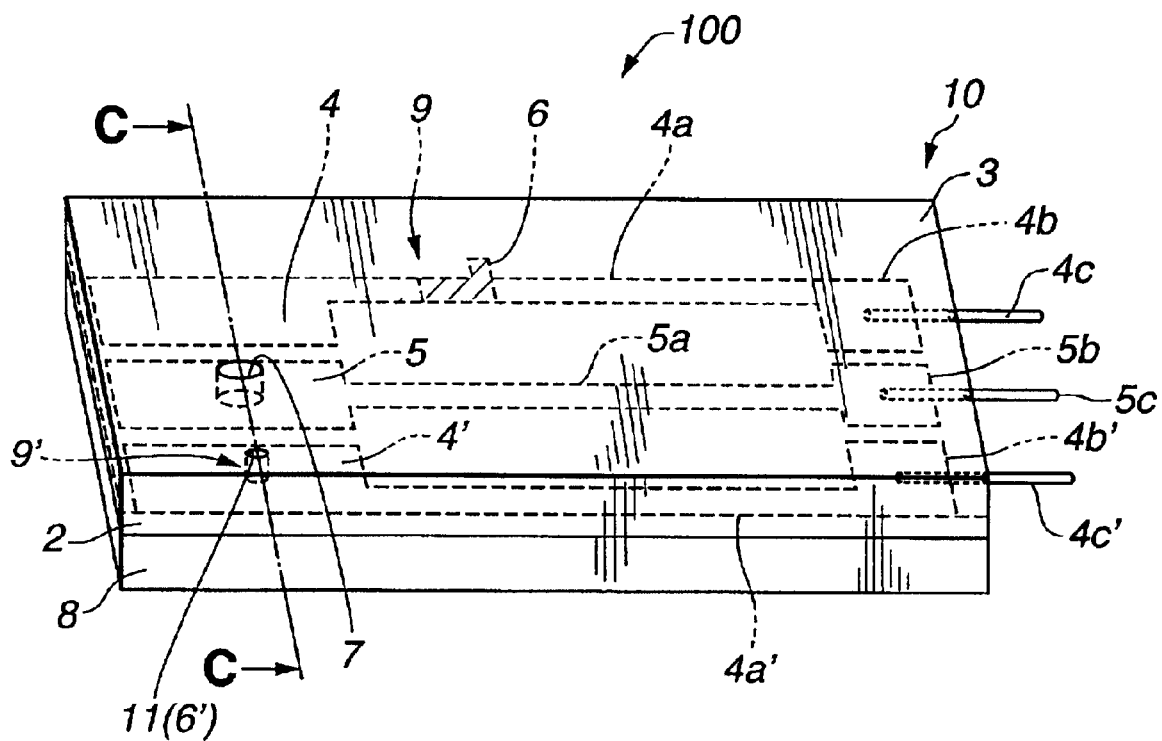
FIG. 12(a) is a perspective view of the gas sensor 100.
Figure 12B:
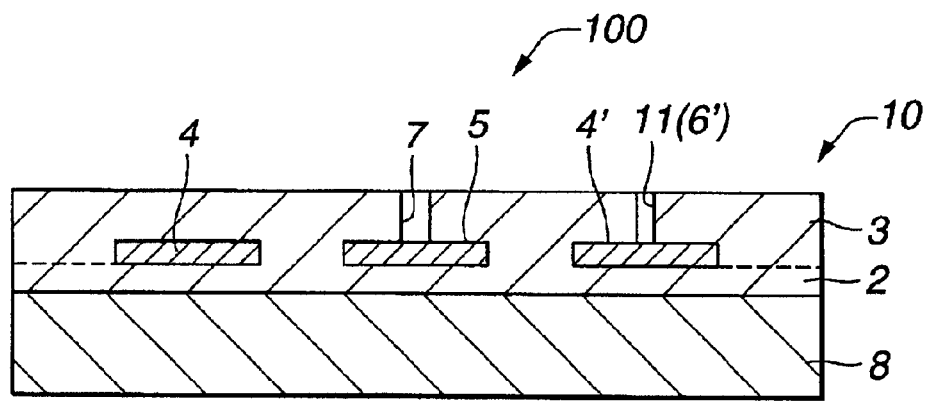
FIG. 12(b) is a cross section taken along lines C—C in FIG. 12(a)

As is seen in FIG. 12(a) and FIG. 12(b) (third modification), there is provided a gas sensor 100. The gas sensor 100 is a modified version of the gas sensor 1 in FIG. 1. Parts of the gas sensor 100 which are common to those of the gas sensor 1 use the same numerals and symbols as those of the gas sensor 1. Explanations are only about the differences. The sensor 100 has a pair of the second cathode 4 and the first cathode 4' which are disposed in such a manner as to share the anode 5. In this embodiment, the anode 5 is disposed substantially in the middle of and in a widthwise direction of the sensor element 2, while each of the second cathode 4 and the first cathode 4' are disposed adjacent to the anode 5 on one of two sides of the anode 5 in the widthwise direction of the sensor element 2. There are also provided pairwise parts such as; a pair of the cathode lead 4a and a cathode lead 4a', a pair of the gas introducing portion 6 and a gas introducing portion 6', and a pair of the terminal 4c and a terminal 4c'. In this constitution in FIG. 12(a), the gas vent 15 as is shown in FIG. 1 is not formed. Like in FIG. 5, the gas diffusion control 9' in FIG. 12(a) has the gas vent 11. The gas vent 11 acts as the gas introducing portion 6', and has a bore diameter which is so adjusted as to introduce the measurement gas under the free diffusion condition. Moreover, as is seen in FIG. 12(b), the gas vent 11 is so formed as to penetrate through the gas blockage 3 and introduce the measurement gas into the first cathode 4'. Like in FIG. 5, the bore diameter of the gas vent 11 in FIG. 12(a) and FIG. 12(b) is formed in a range from 3 $\mu$m to 3,000 $\mu$m.

Figure 13:
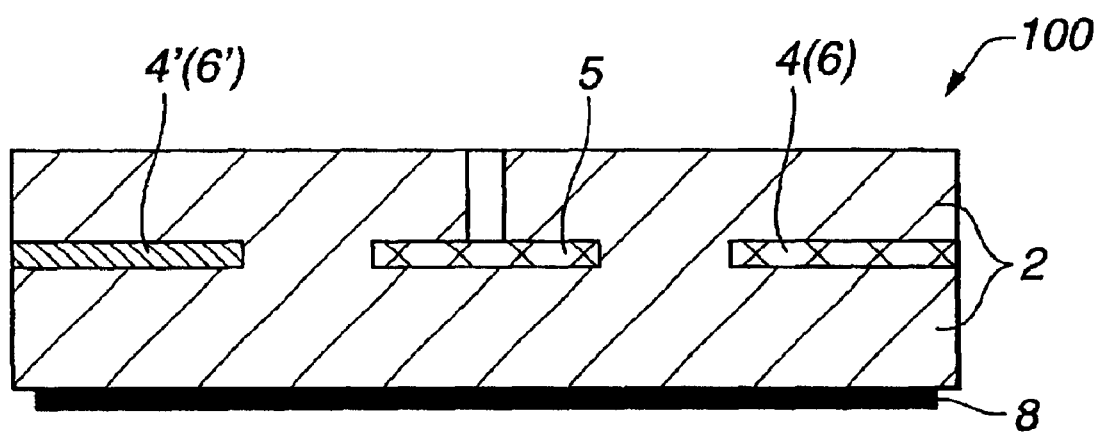
FIG. 13 is a cross sectional view of the gas sensor 100 with a fourth modification.

As is seen in FIG. 13 (fourth modification), there is provided the gas sensor 100 having another type of constitution. In FIG. 13, like in FIG. 12(a) and FIG. 12(b), the gas sensor 100 has a pair of the second cathode 4 and the first cathode 4' which are disposed in such a manner as to share the anode 5. Moreover, each of the first cathode 4' and the second cathode 4 is made of porous material, and is exposed from a side wall of the gas sensor 100 so that the measurement gas can be introduced into the first cathode 4' and the second cathode 4 by way of the exposure. The first cathode 4' and the second cathode 4 are different from each other in size of the porosity. Thereby, diffusing power is made differentiated between the first cathode 4' and the second cathode 4. In other words, each of the first cathode 4' and the second cathode 4 acts as a gas diffusion control by itself.

Figure 14:
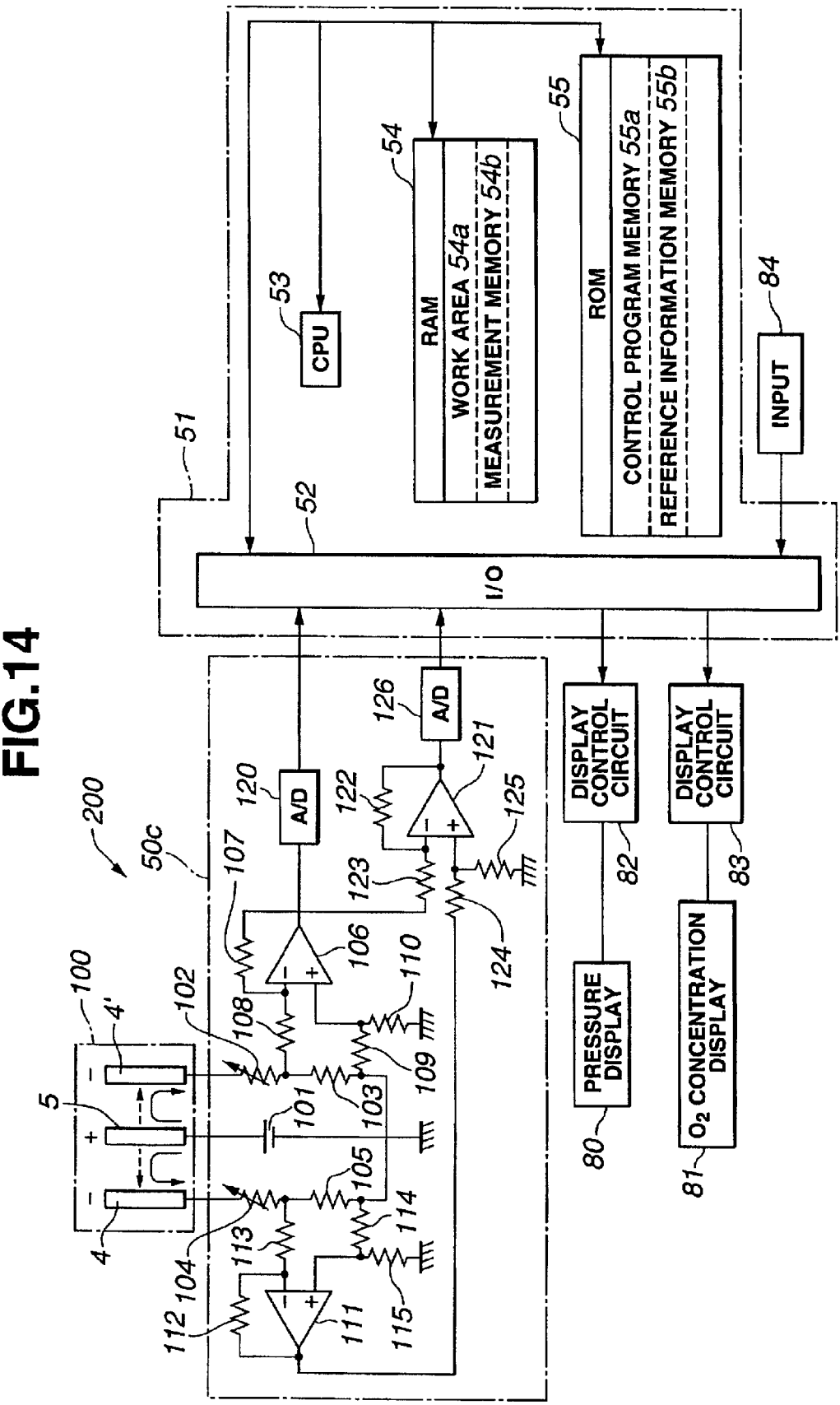
FIG. 14 is a detailed block diagram of an electrical constitution of the gas sensor system using the gas sensor 100 in one of FIG. 12 and FIG. 13.

As is seen in FIG. 14, there is provided a block diagram showing an example of an electrical constitution of a sensor system 200 having the common anode 5 as stated above. Parts of the sensor system 200 in FIG. 14 which are common to those of the sensor system 50 in FIG. 7 use the same numerals and symbols as those of the sensor system 50. Explanations are only about the differences. Specifically, in a peripheral circuit 50c, the anode 5 of the gas sensor 100 is connected to an anode of a constant voltage power supply 101. On the other hand, the first cathode 4' is connected to a cathode (connected to ground) of the constant voltage power supply 101 by way of a variable resistor 102 (or a fixed resistor is allowed) and a resistor 103, while the second cathode 4 is connected to the cathode of the constant voltage power supply 101 by way of a variable resistor 104 (or a fixed resistor is allowed) and a resistor 105.

The oxygen pumping current I' flowing between the anode 5 and the first cathode 4' is inputted to an operation amplifier 106 in a form of a potential difference between both ends of the resistor 103. The operation amplifier 106 constitutes a differential amplifier together with peripheral resistors, namely, a resistor 107, a resistor 108, a resistor 109 and a resistor 110. An output from the operation amplifier 106 is inputted to the microprocessor 51 as a detection signal by way of an A/D converter 120. On the other hand, the oxygen pumping current I flowing between the anode 5 and the second cathode 4 is inputted into an operation amplifier 111 in a form of a potential difference between both ends of the resistor 105. The operation amplifier 111 constitutes a differential amplifier together with peripheral resistors, namely, a resistor 112, a resistor 113, a resistor 114 and a resistor 115. There is provided an operation amplifier 121 which constitutes a differential amplifier together with peripheral resistors, namely, a resistor 122, a resistor 123, a resistor 124 and a resistor 125. The operation amplifier 121 outputs a differential voltage (between output voltage of the operation amplifier 111 and output voltage of the operation amplifier 106) as a detection output of the aforementioned $\Delta I$. Then, the differential voltage is inputted to the microprocessor 51 by way of an A/D converter 126. Also, the output voltage value from the operation amplifier 111 is allowed to be inputted directly to the microprocessor 51 by way of another A/D converter, apart from being inputted to the operation amplifier 121. In other words, information on the pumping current generated at the second cathode 4 is allowed to be inputted to the microprocessor 51 independently.

Based on the oxygen pumping current I' from the operation amplifier 106, the microprocessor 51 determines the oxygen concentration, by referring to the table 210 in FIG. 10(a). Moreover, based on the information from the operation amplifier 121 (namely, $\Delta I=I'-I$), the microprocessor 51 determines the pressure P of the measurement gas, by referring to the table 216 in FIG. 10(d). Furthermore, based on the oxygen pumping current I of the second cathode 4 and the oxygen pumping current I' of the first cathode 4' which are inputted independently of each other as stated above, the microprocessor 51 determines the pressure P, by referring to tables in FIG. 9 through FIG. 11. The determination method is the same as that described above. In addition, a method of outputting pieces of information on the determined oxygen concentration and the pressure is the same as that above mentioned. Moreover, the sensor system 200 can be a gas sensor unit capable of measuring altitude (as an altimeter) and atmospheric pressure (as a barometer) provided that the pressure information of the measurement gas calculated by the sensor system 200 are outputted as altitude information at a measurement position, and atmospheric pressure information. Still furthermore, if the pressure of the measurement gas is known, it can be converted to the altitude value with ease, based on the information on the pressure of the measurement gas and based on the information on atmospheric oxygen concentration, by using known conversion formulas. It is preferable to provide such pressure-to-altitude conversion table.

EXAMPLE 1

A gas sensor is obtained that has a configuration shown in FIG. 8 in the following method:

Zirconia ($ZrO_2$) is subjected to a solution treatment with 10 mol % of yttria ($Y_2O_3$) for stabilization, to thereby form a powder. Then, the thus obtained powder is mixed with about 5% of resin (in this example 1, acrylic resin), for granulation into a powder that is capable of being subjected to powder pressing. Then, the thus obtained powder is subjected to pressing with a press machine, to thereby form the sensor element 2 (see FIG. 8) having about 0.8 mm in thickness and about 7 mm in diameter. Then, Pt electrodes are printed both on upper and lower sides of the sensor element 2, followed by firing at about 1,500° C. in an atmosphere for two hours. Then, a material made of alumina mixed with resin (in this example 1, acrylic resin) is pressed, and a hole having a diameter of 50 $\mu$m is formed substantially in the center of the material, to thereby prepare a fired housing (gas blockage 3, see FIG. 8). An upper portion of the thus prepared housing (gas blockage 3) is formed with the heater element 8 for heating the gas sensor to 500° C. Then, the housing (gas blockage 3) is adhered, using a glass sealant and the like, to an upper surface of the sensor element 2 that has the above mentioned Pt electrode, to thereby form the constitution of the gas sensor shown in FIG. 8. In the following descriptions, the thus obtained gas sensor is referred to as a gas sensor A.

There is provided another gas sensor that is to be referred to as a gas sensor B hereinafter. There is provided the porous body 12 in a hole of the above housing (gas blockage 3) of the gas sensor B. The porous body 12 is formed by mixing alumina powder (mean grain diameter of 0.3 $\mu$m) with a small amount of glass, followed by firing. A scanning electron microscope determines the hole diameter of the porous body 12 in a range from 3,000 to 6,000 angstrom (0.3 $\mu$m to 0.6 $\mu$m). Then, a voltage direct current 0.8 VDC is applied to the gas sensor A and the gas sensor B.

Figure 15:
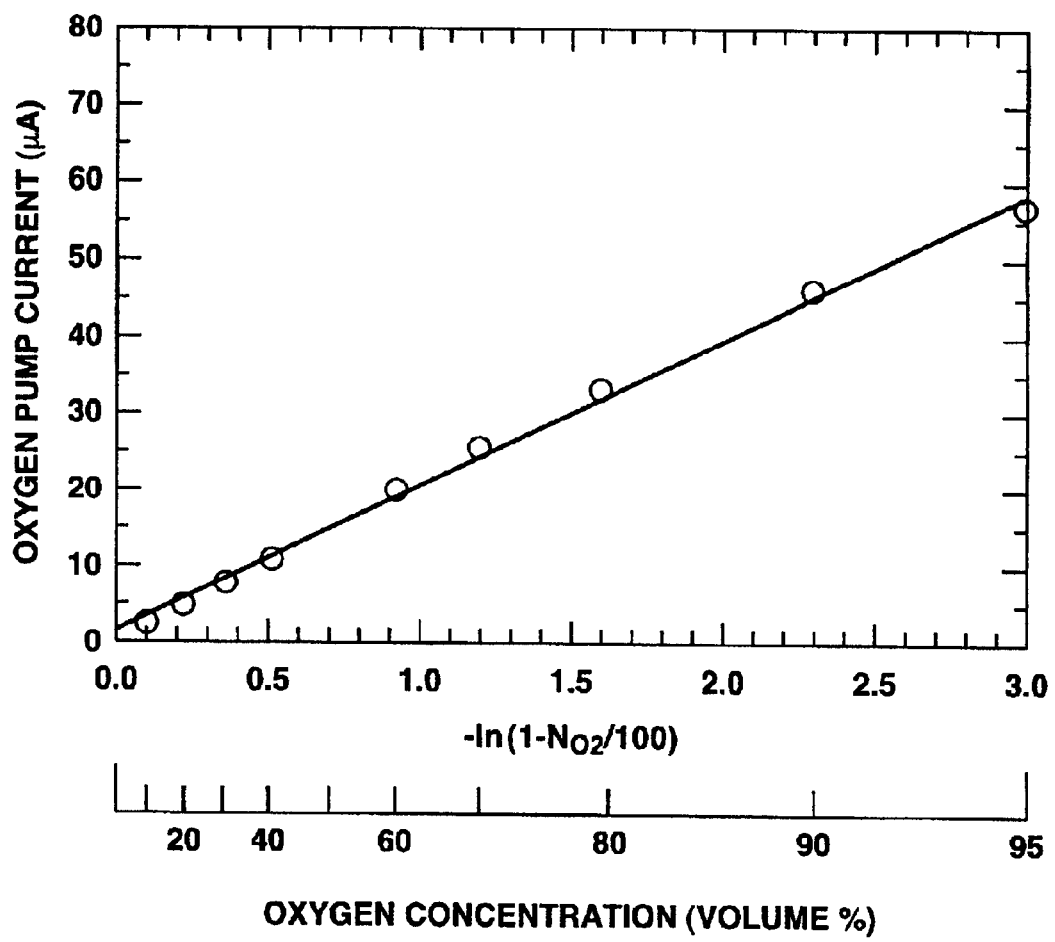
FIG. 15 is a graph showing the oxygen concentration (volume %) relative to the oxygen pumping current ($\mu A$)

As is seen in FIG. 15, the output current (A) of the gas sensor relative to the oxygen concentration ($N_{O2}$ volume %) is linearly changeable to "$-\ln(1-N_{O2}/100)$." In FIG. 15, the ordinate is a value of oxygen pumping current ($\mu$A), while the abscissa is a value of "$-\ln(1-N_{O2}/100)$" in negative.

Figure 16:
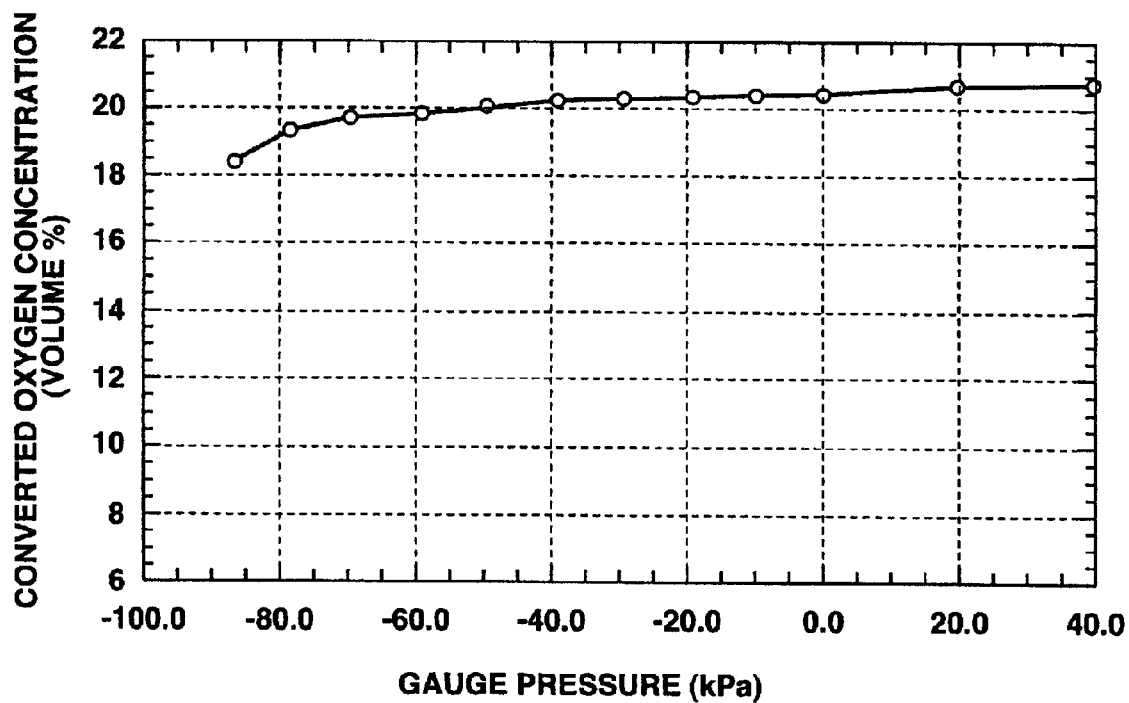
FIG. 16 is a graph showing a gauge pressure (kPa) relative to a converted oxygen concentration (volume %) at the first cathode 4'.
Figure 17:
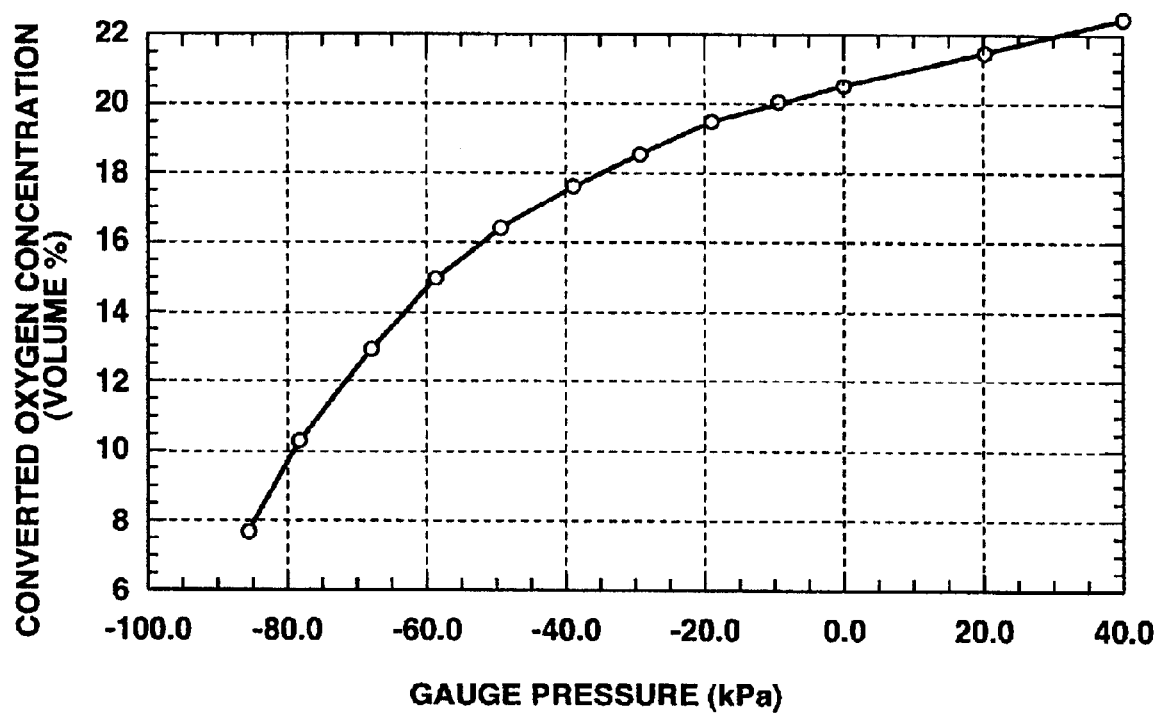
FIG. 17 is a graph showing a gauge pressure (kPa) relative to the converted oxygen concentration (volume %) at a second cathode 4.

Then, the gas sensor A and the gas sensor B are subjected to a pressure dependency test under a constant oxygen concentration (atmospheric pressure: $N_{O2}$: 21 volume %). As is seen in FIG. 16, the gas sensor A is not so influenced by the pressure change. Contrary to this, as is seen in FIG. 17, the gas sensor B is greatly influenced by the pressure change. Presumed causes of the test results are as follows: In terms of gas diffusion, the gas sensor A having a large diffusion hole {see gas introducing portion 6' in FIG. 8(a)} is dominated by molecular diffusion, while the gas sensor B having a small diffusion hole {see gas introducing portion 6 in FIG. 8(b)} is dominated by Knudsen diffusion that influences oxygen molecular diffusion, thus causing the great pressure dependency to the gas sensor B.

Figure 18:
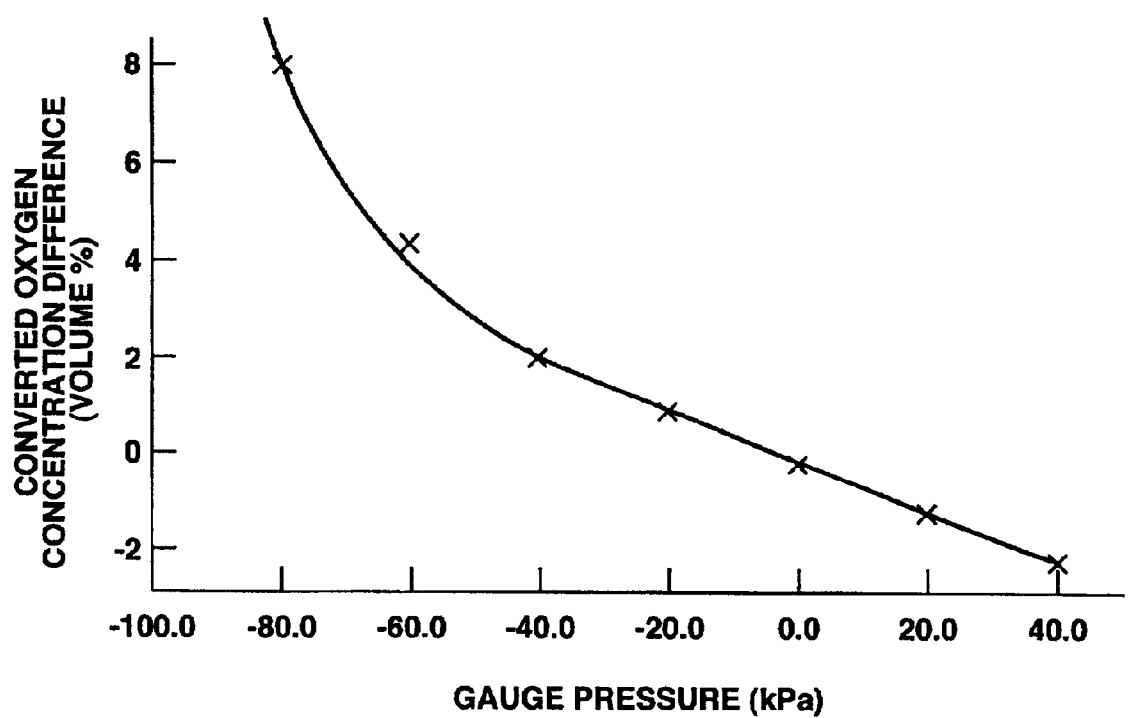
FIG. 18 is a graph showing a gauge pressure (kPa) relative to a converted oxygen concentration difference (volume %) between the first cathode 4' and the second cathode 4.

As is seen in FIG. 18, there is provided a graph showing the detected oxygen concentration difference (volume %) relative to the pressure (gauge pressure in kPa) of the measurement gas. The detected oxygen concentration difference is the difference in output current value between the gas sensor A and the gas sensor B, namely, the different pressure dependency electrodes (second cathode 4 and first cathode 4' in FIG. 8 and the like). As is seen in FIG. 18, the gas sensor A and the gas sensor B under the constant oxygen concentration exhibit substantially a monotonous decrease in output current difference relative to the increase in the pressure of the measurement gas. Therefore, the output current difference evidently contributes toward obtaining the pressure of the measurement gas.

EXAMPLE 2

A gas sensor is obtained that has a configuration shown in FIG. 13 (the anode 5 shared by the second cathode 4 and the first cathode 4') in the following method:

Zirconia ($ZrO_2$) is subjected to a solution treatment with 10 mol % of yttria ($Y_2O_3$) for stabilization, to thereby form a powder. Then, the thus obtained powder is mixed with about 8% of resin (in this example 2, acrylic resin). Then, a slurry added by a solvent is subjected to a doctor blade so as to form a sheet of 0.8 mm. Then, the sheet is cut into a square having a side of 5 mm, to thereby form the sensor element 2. As is seen in FIG. 13, the sensor element 2 is prepared two in number.

On one sheet of the sensor element 2, a Pt electrode pattern is printed. The Pt electrode pattern is the one that has two cathode (namely, the first cathode 4' and the second cathode 4) having different porosity constitutions from each other, and one common anode (namely, the anode 5). The thus formed first cathode 4' and the second cathode 4 have, respectively, the gas introducing portion 6' and the gas introducing portion 6. As is seen in FIG. 13, at one detecting portion, namely, the second cathode 4 and the anode 5, it is only the Pt powder that is printed. The porosity dimension of the second cathode 4 is in a range from 3,000 to 6,000 angstrom (0.3 $\mu$m to 0.6 $\mu$m), same as that of the porous body 12 (gas introducing portion 6) in example 1 above. At the other detecting portion, namely, the first cathode 4', the Pt powder is mixed with one of alumina and zirconia by about 10% weight for printing. Such alumina or zirconia has a mean grain diameter in a range from 1 μm to 10 μm. The porosity dimension of the first cathode 4' is 5 μm. The sheet (sensor element 2) with the thus printed electrodes has a back side on which the heater 8 is printed with the Pt electrode, in order to heat the gas sensor 100.

The thus obtained zirconia sheet (sensor element 2) is laminated with the other zirconia sheet (sensor element 2) in such a manner that the first cathode 4', the second cathode 4 and the anode 5 face the other zirconia sheet. Then, the thus laminated two sensor elements 2 are subjected to firing at 1,500° C. for two hours, to thereby form the gas sensor (hereinafter referred to as "gas sensor C") as is seen in FIG. 13. In this manner, the thus integrated gas sensor C is provided with two cathodes, that is, the first cathode 4' and the second cathode 4, so that the diffusing power becomes greatly differentiated at gas diffusion controls. Moreover, the gas sensor C has the anode 5 that is common to the first cathode 4' and the second cathode 4. Then, a voltage is applied to each of the first cathode 4' and the second cathode 4, to thereby obtain the oxygen pumping current from one of the respective first cathode 4' and second cathode 4. Moreover, an output-to-pressure data is obtained, namely, output current values (oxygen pumping current from each of the first cathode 4' and the second cathode 4) relative to the pressure of the measurement gas. In this example 2, like in the example 1, the first cathode 4' (namely, one of alumina and zirconia mixed) having a large bore diameter of porosity exhibits a very small pressure dependency, as is seen in FIG. 16. Contrary to this, the second cathode 4 exhibits the oxygen pumping current value that is largely dependent on pressure, as is seen in FIG. 17. Each of FIG. 16 and FIG. 17 has the ordinate for showing the oxygen concentration converted from the output current value (volume %), and the abscissa for showing the gauge pressure (kPa).

Summarizing the example 1 and example 2 above, the constitutions of the gas sensors shown in FIG. 8 and FIG. 13 enable measurement of the gas pressure.

Although the invention has been described above by reference to certain embodiments of the invention, the invention is not limited to the embodiments described above. Modifications and variations of the embodiments described above will occur to those skilled in the art, in light of the above teachings. The scope of the invention is defined with reference to the following claims.

What is claimed is:

1. A gas sensor comprising:
a sensor element formed of a solid electrolyte having an oxygen ion conductivity;
a plurality of cathodes and an anode, each formed of a porous metal material and each formed on the sensor element, to produce a pumping current reflecting a concentration of a detection component in a measurement gas when a predetermined voltage is applied between the cathodes and the anode, the detection component comprising oxygen, the measurement gas contacting the cathodes; and
a plurality of means for controlling a gas diffusion of the measurement gas in such a manner that the oxygen pumping current varies in accordance with a pressure of the measurement gas, the measurement gas moving from a measurement atmosphere toward the cathodes by way of the means for controlling the gas diffusion, to thereby obtain information on the pressure of the measurement gas based on the oxygen pumping current, wherein the cathodes are provided as different pressure dependency electrodes, each of the different pressure dependency electrodes corresponding to one of the respective means for controlling the as diffusion in which the means for controlling the as diffusion are so adjusted in terms of gas diffusion resistance as to make a difference between the corresponding different pressure dependency electrodes in terms of pressure dependency of the oxygen pumping current to be outputted; and in which the information on the pressure of the measurement gas is generated based on the oxygen pumping current outputted from each of the different pressure dependency electrodes.

2. The gas sensor as claimed in claim 1, in which the means for controlling the gas diffusion is a porous body having pores with bore diameters in a range from 0.01 into 1 m.

3. The gas sensor as claimed in claim 2, in which the diffusion which is so controlled by the means for controlling the gas diffusion as to vary the oxygen pumping current in accordance with the pressure of the measurement gas is Knudsen diffusion.

4. The gas sensor as claimed in claim 3, in which the porous metal material of each of the cathode and the anode is a platinum material which is one of platinum and platinum alloy.

5. The gas sensor as claimed in claim 3, in which the porous metal material of the anode is a palladium material which is one of palladium and palladium alloy.

6. The gas sensor as claimed in claim 5, in which the oxygen pumping current corresponds to the pressure of the measurement gas substantially on one-to-one basis when the concentration of the oxygen contained in the measurement gas is constant.

7. The gas sensor as claimed in claim 1, in which information on the concentration of the oxygen of the measurement gas, in addition to the information on the pressure of the measurement gas, is obtained based on the oxygen pumping current outputted from each of the different pressure dependency electrodes.

8. The gas sensor as claimed in claim 1, in which the different pressure dependency electrodes comprise a first cathode and a second cathode, the outputted oxygen pumping current being more pressure dependent at the second cathode than at the first cathode, and in which a difference in the outputted oxygen pumping current between the first cathode and the second cathode is outputted as the information on the pressure of the measurement gas.

9. The gas sensor as claimed in claim 8, in which the outputted oxygen pumping current at the first cathode is obtained as the information on the concentration of the oxygen of the measurement gas.

10. The gas sensor as claimed in claim 1, in which each of the means for controlling the gas diffusion corresponding to one of the respective cathodes is formed with a gas vent so as to introduce the measurement gas to one of the respective cathodes, and in which a diffusing power for the measurement gas is adjusted in accordance with a bore diameter of the gas vent.

11. The gas sensor as claimed in claim 10, in which the different pressure dependency electrodes comprise a first cathode and a second cathode, wherein the gas vent of the means for controlling the gas diffusion of the first cathode has the bore diameter in a range from 3 μm to 3,000 μm, the outputted oxygen pumping current being less pressure dependent at the first cathode than at the second cathode.

12. The gas sensor as claimed in claim 11, in which the diffusion at the means for controlling the gas diffusion of the first cathode is a free diffusion, and in which the oxygen pumping current detected at the gas diffusion control of the first cathode corresponds to the concentration of the oxygen of the measurement gas substantially on one-to-one basis.

13. The gas sensor as claimed in claim 1, in which the gas sensor is a pressure sensor.

14. The gas sensor as claimed in claim 13, in which the anode of the pressure sensor is common to the plurality of the cathodes.

15. A sensor unit comprising a pressure sensor, the pressure sensor comprising:

a sensor element formed of a solid electrolyte having an oxygen ion conductivity;

a plurality of cathodes and an anode, each formed of a porous metal material and each formed on the sensor element, to produce a pumping current reflecting a concentration of a detection component in a measurement gas when a predetermined voltage is applied between the cathodes and the anode, the detection component comprising oxygen, the measurement gas contacting the cathodes; and a plurality of means for controlling a gas diffusion of the measurement gas in such a manner that the oxygen pumping current varies in accordance with a pressure of the measurement gas, the measurement gas moving from a measurement atmosphere toward the cathodes by way of the means for controlling the gas diffusion, to thereby obtain information on the pressure of the measurement gas based on the oxygen pumping current, in which the sensor unit generates and outputs information on an atmospheric pressure and an altitude based on the information on the pressure obtained by the pressure sensor, wherein the cathodes are provided as different pressure dependency electrodes, each of the different pressure dependency electrodes corresponding to one of the respective means for controlling the gas diffusion; in which the means for controlling the gas diffusion are so adjusted in terms of gas diffusion resistance as to make a difference between the corresponding different pressure dependency electrodes in terms of pressure dependency of the oxygen pumping current to be outputted; and in which the information on the pressure of the measurement gas is generated based on the oxygen pumping current outputted from each of the different pressure dependency electrodes.

16. The sensor unit as claimed in claim 15, in which the anode of the pressure sensor is common to the plurality of the cathodes.

* * * * *